(12) United States Patent
Gunkel et al.

(10) Patent No.: US 8,726,434 B2
(45) Date of Patent: May 20, 2014

(54) SUPPORT APPARATUS AND PATIENT SUPPORT TABLE AS WELL AS MEDICAL DEVICE

(75) Inventors: Joachim Gunkel, Lorch (DE); Hans-Peter Hollenbach, Eggolsheim (DE); Ludwig Kreischer, Dormitz (DE); Markus Petsch, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1062 days.

(21) Appl. No.: 12/565,946

(22) Filed: Sep. 24, 2009

(65) Prior Publication Data
US 2010/0071131 A1    Mar. 25, 2010

(30) Foreign Application Priority Data
Sep. 30, 2008 (DE) .................. 10 2008 049 711

(51) Int. Cl.
*A47B 13/00*  (2006.01)
(52) U.S. Cl.
USPC ............. 5/601; 5/600; 5/604; 5/943; 5/722; 5/723
(58) Field of Classification Search
USPC .............. 5/601, 600, 604, 943, 722, 723; 378/208, 209
See application file for complete search history.

(56) References Cited

U.S. PATENT DOCUMENTS

| | | | | |
|---|---|---|---|---|
| 2,033,779 A * | 3/1936 | Monk | | 5/627 |
| 4,550,681 A * | 11/1985 | Zimmer et al. | | 118/410 |
| 5,514,220 A * | 5/1996 | Wetmore et al. | | 134/22.18 |
| 5,766,637 A * | 6/1998 | Shine et al. | | 424/497 |
| 7,216,383 B2 * | 5/2007 | Heinl et al. | | 5/601 |
| 2007/0039101 A1 | 2/2007 | Luginbuhl et al. | | |
| 2008/0250565 A1 * | 10/2008 | Timmerman et al. | | 5/621 |
| 2010/0071131 A1 * | 3/2010 | Gunkel et al. | | 5/600 |
| 2010/0080344 A1 * | 4/2010 | Schilling et al. | | 378/37 |
| 2010/0128843 A1 * | 5/2010 | Tita | | 378/37 |
| 2011/0047706 A1 * | 3/2011 | Hiebert | | 5/623 |
| 2011/0074407 A1 * | 3/2011 | Ladebeck | | 324/261 |
| 2011/0173753 A1 * | 7/2011 | Luginbuhl et al. | | 5/601 |

OTHER PUBLICATIONS

Engelhard et al., "MRI-guided prostate biopsy in two different standard 1.5 T scanners using an endorectal biopsy device", (Abstract) Proc. Intl. Soc. Mag. Reson. Med. 14 (2006), pp. 1446.

* cited by examiner

*Primary Examiner* — Robert G Santos
*Assistant Examiner* — David E Sosnowski

(57) ABSTRACT

The invention relates to a support apparatus on which a patient can be supported in a comfortable and secure manner for the preparation for an examination and for the examination, in particular an endorectal biopsy. The support apparatus comprises a sliding apparatus connected to a bearing substructure and is supported in a displaceable manner on the sliding apparatus so that it can be moved partially beyond the substructure connected to the sliding apparatus. The support apparatus also comprises a cutout. The invention also relates to a patient support table comprising a connecting apparatus to connect the patient support table to the support apparatus and serving as a bearing substructure for the support apparatus. A medical device, in particular an MR device, is also disclosed comprising a patient tunnel and the patient support table that can be introduced into the patient tunnel.

14 Claims, 2 Drawing Sheets

SUPPORT APPARATUS AND PATIENT SUPPORT TABLE AS WELL AS MEDICAL DEVICE

CROSS REFERENCE TO RELATED APPLICATIONS

This application claims priority of German application No. 10 2008 049 711.8 filed Sep. 30, 2008, which is incorporated by reference herein in its entirety.

FIELD OF THE INVENTION

The invention relates to a support apparatus, a patient support table and a medical device.

BACKGROUND OF THE INVENTION

In order to be able to perform examinations of the lower abdomen in a specific manner, medical examination apparatuses, such as a biopsy apparatus or local transmit and/or receive apparatuses, for example ultrasound heads or a local coil for magnetic resonance applications, are inserted rectally or vaginally into the lower abdomen of a patient to be examined, in order to be positioned as close as possible to the organ to be examined, e.g. the prostate, the ovaries, the rectum/bowel or the uterus.

An endorectal or endovaginal biopsy apparatus is used to take tissue samples from the organ to be examined, which are then examined for possibly cancerous substances. It is advantageous here to know the site from which the tissue was taken precisely, for example in order to be able to apply any necessary therapy in a specific manner. To this end the biopsy is monitored using medical imaging technology.

The medical imaging technology primarily known for such monitoring is sonography but sectional image methods such as computed tomography (CT) or magnetic resonance tomography, in some instances combined with functional Positron Emission Tomography (PET), are increasingly used. MRT in particular offers particularly good soft tissue contrast resolution as far as the latter methods are concerned.

To monitor the biopsy using such a sectional image method the patient is conveyed on a patient support table into the generally tunnel-type examination region of the corresponding medical device, with the endorectal or endovaginal examination apparatus already positioned in the lower abdomen.

Further examinations of the lower abdomen can also be performed with local transmit and/or receive apparatuses. Special local coils, endorectal or endovaginal coils are known in particular for magnetic resonance applications, which can be used to take particularly high-resolution recordings of the lower abdomen and which can also be used for magnetic resonance spectroscopy. To this end the local coils are inserted into the lower abdomen and the patient is introduced into a magnetic resonance device on a patient table.

To make the rectum more accessible, the patient is supported on his/her front (prone) on a respective patient support table and introduced thus into the respective examination space both for the biopsies described above, which are monitored using medical sectional image methods, and for examinations with the above-mentioned special local coils. However this position is not very comfortable for the patient. More protracted procedures, such as a prostate biopsy with up to 2 hours examination time, cannot be tolerated for longer periods by elderly patients in particular and the patient starts to feel ill at ease, agitated or even short of breath. As well as the lack of comfort for the patient, it may also result in patient movement and therefore unwanted motion artifacts in the images.

At the conference of the "International Society for Magnetic Resonance in Medicine", ISMRM 2006, in Seattle, Wash., USA a two-part apparatus was disclosed, which allows a patient to be supported on his/her back (supine) on the patient support table for am MR-monitored biopsy (Abstract "MRI-guided prostate biopsy in two different standard 1.5 T scanners using an endorectal biopsy device", Proc. Intl. Soc. Mag. Reson. Med. 14 (2006), page 1446; and associated poster). However the patient must still slide into the patient tunnel feet first on the patient support table until an assistant standing behind the magnet of the magnetic resonance device can grasp and hold up the patient's legs. The helper then inserts a support part arranged at this end of the magnetic resonance device and connects it to the patient support table. A support system made up of two separate parts (patient support table and support part) is thus formed. The patient's legs are positioned on the support part so that an endorectal examination apparatus can be inserted. This procedure requires effort from both the assistant and the patient. More effort is required, the heavier the patient's legs are and depending on how much the patient can or must help the assistant in the process. The support part proposed at ISMRM 2006, which is introduced from the rear into the magnetic resonance device, can only be moved to a certain degree into the magnetic resonance device. In particular it is not possible to convey the patient support table and therefore the patient out of the magnetic resonance device after the examination without removing the support part again first. This extends the examination period.

SUMMARY OF THE INVENTION

One object of the invention is therefore to specify a support apparatus on which on which a patient can be supported in a comfortable and secure manner both for the preparation for an examination and for the examination, in particular of the lower abdomen, itself. A further object is to specify an improved patient support table and a medical device with such a patient support table, with which preparation can be made for an examination and the examination itself can be performed in a simple, secure and efficient manner that is comfortable for the patient in a patient tunnel of the medical device.

The first-mentioned object is achieved by a support apparatus as claimed in the claims. For this the support apparatus, on which a patient can be supported on his/her back (supine), comprises a sliding apparatus, which can be connected to a bearing substructure. The support apparatus is supported in a displaceable manner on the sliding apparatus so that it can be moved at least partially beyond the substructure connected to the sliding apparatus. The support apparatus also comprises a cutout.

With the inventive support apparatus it is possible in a simple manner to support a patient securely on the support apparatus, for example while the overall support apparatus is borne by the substructure. It is this possible for the patient to climb up onto the support apparatus without particular assistance. It will thus be sufficient generally for an assistant to provide a small amount of help as the patient climbs up onto the support apparatus. To prepare for an examination, particularly of the lower abdomen, the patient can be displaced on the support apparatus in relation to the substructure of the support apparatus. This facilitates access to the patient, as the substructure is no longer in the way.

It is advantageously possible to move the support apparatus beyond the substructure at least so far that the cutout is adjacent to the substructure. With the support apparatus in this position it is possible to access the patient directly adjacent to the substructure through the cutout.

In one advantageous embodiment the support apparatus around the cutout comprises a securing apparatus to secure a medical examination apparatus. The examination apparatus, for example a biopsy apparatus or a local coil apparatus, can thus be held on the support apparatus and can reach a patient to be examined on the support apparatus in a secure manner through the cutout.

According to the invention the second-mentioned object is achieved by a patient support table, which comprises a connecting apparatus to connect the patient support table to a support apparatus as described above, and thus serves as a bearing substructure for the support apparatus as well as by a medical device with a patient tunnel and a similarly above-mentioned patient support table that can be introduced into the patient tunnel. The above-mentioned advantages apply correspondingly.

BRIEF DESCRIPTION OF THE DRAWINGS

Further advantages and details of the present invention will emerge from the exemplary embodiments described below and based on the drawings. The examples listed do not represent any restriction of the invention. In the drawings.

Identical parts are shown with the same reference characters in all the figures.

DETAILED DESCRIPTION OF THE INVENTION

Figure 1:
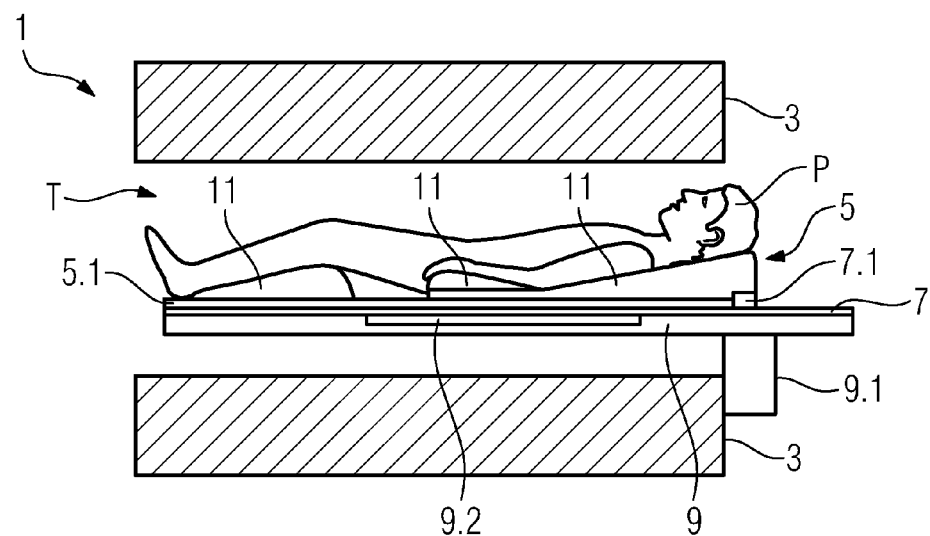
FIG. 1 shows a schematic diagram of a medical device with a patient support table and a support apparatus in a first position.
Figure 2:
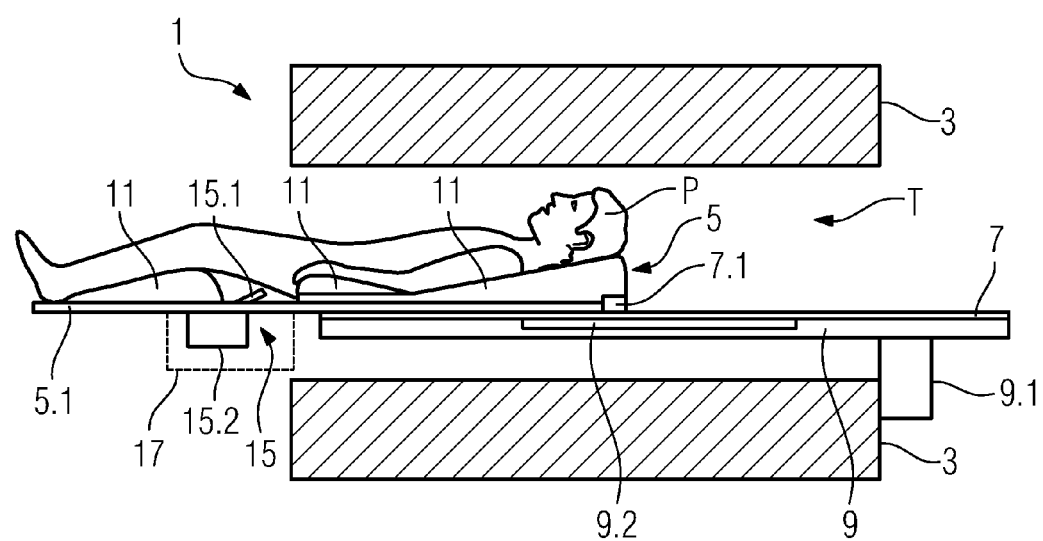
FIG. 2 shows a schematic diagram of a medical device with a patient support table and a support apparatus in a second position.

FIGS. 1 and 2 show schematic diagrams of a medical device 1 with a patient tunnel T and a patient support table 9 that can be conveyed by means of a conveyor apparatus 9.1 from the front of the medical device into the patient tunnel T. The medical device is for example a magnetic resonance device with a magnet unit 3, which encloses the patient tunnel T radially to the axis of the patient tunnel T. In other exemplary embodiments the medical device 1 can also be a computed tomography device or a PET device, the gantry and/or detector of which encloses the patient tunnel.

In FIG. 1 the patient support table 9 holds a support apparatus 5. The support apparatus 5 here comprises a support board 5.1 and a sliding apparatus 7, which is connected to the patient support table 9 as a bearing substructure by way of a connecting apparatus 9.2. The connecting apparatus 9.2 here is configured such that the support apparatus 5 is connected in a detachable manner to the bearing patient support table 9, so that the support apparatus 5 can be removed from the patient support table 9. It is thus also possible to use the medical device 1 in the usual manner without the support apparatus 5.

The connecting apparatus 9.2 is for example advantageously configured as an interchangeable board of the patient support table 9. Such interchangeable boards for patient support tables are known, for example from the MR devices MAGNETOM Symphony or MAGNETOM Avanto available from Siemens AG, and allow fast and easy refitting of the patient support table, for example even with different tops.

The detachability of the support apparatus 5 from the substructure 9 means it is possible to prepare a patient for examination outside the examination space where the medical device 1 is located, in that said patient can for example "try out" the support apparatus 5 in a preparation space.

In FIG. 1 the support apparatus 5 is in a first position relative to the patient support table 9, in which the support apparatus 5 does not project beyond the patient support table 9 at any point. In this position the patient support table 9 can be conveyed easily into any possible horizontal position even without the support apparatus 5, without the possibility of collision with the medical device 1 or a patient P on the support apparatus being exposed to any risk. The patient support table 9 can also be conveyed vertically with the support apparatus 5 in the first position, when the patient support table 9 is located in front of the medical device outside the patient tunnel T. The patient support table 9 together with the support apparatus 5 can for example be lowered so that a patient can climb onto the support apparatus 5 and position him/herself there more easily. Because the support apparatus 5 is embodied as an integral part, a patient can be supported simply and in one step on the support apparatus 5, without in particular requiring the assistance of a person performing the examination.

The support apparatus 5 advantageously comprises cushions or pads 11.1, 11.2, 11.3 to support the patient P comfortably. The support apparatus 5 here is advantageously configured in such a manner that a patient P supported thereon is held in the Steinschnitt position.

The support apparatus 5 can be displaced on the sliding apparatus 7. It is sufficient here for the support apparatus 5 to be able to be moved by hand, e.g. by a person performing the examination. Alternatively a motor drive can also be used, in which case compatibility with the medical device 1, for example compatibility with a magnetic resonance device 1, should be ensured.

The support apparatus 5 can be moved by means of the sliding apparatus 7 in particular at least partially beyond the substructure 9, in this instance the patient support table 9, connected to the sliding apparatus 7. In this process the support apparatus 5 can advantageously be displaced at least so far into a second position beyond the patient support table 9 that the foot half of the support apparatus 5 projects beyond the substructure 9. In this second position therefore the legs of a patient P supported on the support apparatus 5 are displaced backward out of the patient tunnel T. In some instances in this position the buttocks of the patient P are also already displaced at least partially backward out of the patient tunnel T.

In order to prevent the displacement of the support apparatus 5 on the sliding apparatus 7 temporarily and instead to stop the support apparatus 5 in a certain position in relation to the substructure 9, the support apparatus 5 has a stop apparatus 7.1 to stop the support apparatus 5 temporarily in relation to the sliding apparatus 7. The stop apparatus 7 here is configured in such a manner that it can stop the support apparatus 5 in a releasable manner in the described first and second positions at least.

The stop apparatus 7.1 used can be for example a stopper that can be connected securely to the sliding apparatus 7 or the substructure 9 and the support apparatus 5 and detached again at different points over the length of the sliding apparatus 7 and prevents sliding on the sliding apparatus 7 or a detachable latching mechanism, e.g. between the support apparatus 5 and the sliding apparatus 7, which allows the support apparatus 5 to latch in a detachable manner at certain positions.

By conveying the patient support table 9 to the rear end of the patient tunnel T and displacing the support apparatus 5 by means of the sliding apparatus 7 in a direction out of the patient tunnel into the second position, it is possible to position the support apparatus 5 in relation to the medical device such that at least the foot half of the support apparatus 5 is freely accessible at the rear, outside the medical device 1, as shown in FIG. 2.

In this position an examination apparatus 15 can be attached to the support apparatus 5 without having to move a patient on the support apparatus 5. This is explained in more detail below with reference to FIG. 4.

Figure 3:
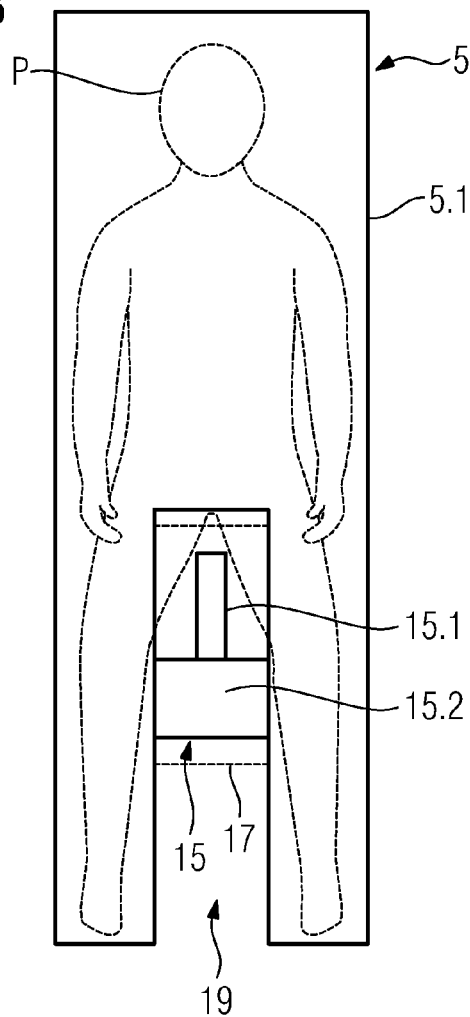
FIG. 3 shows a schematic diagram of a support apparatus viewed from above and FIG. 4 shows a schematic diagram of the support apparatus in the medical device viewed from the front.

As shown in FIG. 3, the foot half of the support apparatus 5 has a cutout 19. The cutout here is arranged centrally over the width of the support apparatus 5. In particular the cutout 19 is arranged on the support apparatus 5 in such a manner that the cutout 19 allows access through the support board 5.1 of the support apparatus 5 to the rear end of a patient P supported on the support apparatus, in particular to body openings at the rear end. To illustrate this, a patient P is shown with a broken line in FIG. 3.

The cutout 19 advantageously runs over the length of the support apparatus 5 to the center of the support apparatus 5, where the rear end of a patient P supported on the support apparatus 5 is approximately located. In the second position described above the support apparatus 5 is therefore displaced so far over the bearing substructure 9, in this instance the patient support table 9, that the cutout 19 is adjacent to the substructure 9 in a horizontal plane.

For particularly easy access to the rear end of the patient P, the cutout 19 advantageously also runs over the length of the support apparatus 5 to the foot end of the support apparatus. This allows access to the patient supported on the support apparatus 5 through the cutout 19 not only from below the support apparatus 5 but also from the foot end of the support apparatus 5.

The cutout 19 here is advantageously configured as a slot in the foot half of the support apparatus 5. This means that the cutout 19 is easy to produce and also particularly easy to see into.

Possible dimensions of the cutout 19 here are for example a width of at least 10 cm, typically 15 cm or more. The width of the cutout 19 here is at least as large as the width of an examination apparatus 15. The length of the cutout 19 is advantageously between 50 cm and 100 cm, e.g. corresponding to the expected leg length of a patient to be examined. A typical length of the cutout is therefore more than 80 cm for example.

As shown in FIG. 2, a medical examination apparatus 15 can be positioned in the cutout 19. The examination apparatus 15 here has an apparatus 15.1 that can be inserted endorectally and/or endovaginally into the lower abdomen of the patient P and a holding and guiding apparatus 15.2 to hold and guide the insertable apparatus 15.1. Such holding and guiding apparatuses 15.2 for endorectally or endovaginally insertable medical apparatuses are known (see for example the abstract and poster "MRI-guided prostate biopsy in two different standard 1.5 T scanners using an endorectal biopsy device", Proc. Intl. Soc. Mag. Reson. Med. 14 (2006), page 1446 cited above). They will therefore not be described in more detail here and it should simply be pointed out that the holding and guiding apparatuses 15.2 for use with a magnetic resonance device must be embodied as MR-compatible, i.e. in particular non-magnetic.

The examination apparatus 15 can be for example a biopsy apparatus 15 with a biopsy needle 15.1 or, where the medical device 1 is a magnetic resonance device, a local coil apparatus 15 with a local coil 15.1. With such a biopsy apparatus 15 it is possible to perform in particular endorectal biopsies of the prostate or the rectum/bowel with simultaneous image monitoring by means of the medical device 1 in a comfortable, and therefore efficient manner, both for the patient and for the user performing the biopsy due to the arrangement in the cutout 19. Endovaginal biopsies, e.g. of the uterus or ovaries, are also facilitated with the support apparatus 5 and the examination apparatus 15, thereby accelerating the examination generally.

In one embodiment, wherein the medical device 1 is a magnetic resonance device 1, the examination apparatus 15 can advantageously comprise an apparatus 15.1 that can be inserted endorectally and/or endovaginally into the lower abdomen of a patient on the support apparatus 5, said apparatus 15.1 comprising both a biopsy needle and a local coil for precise image monitoring for the biopsy.

Figure 4:
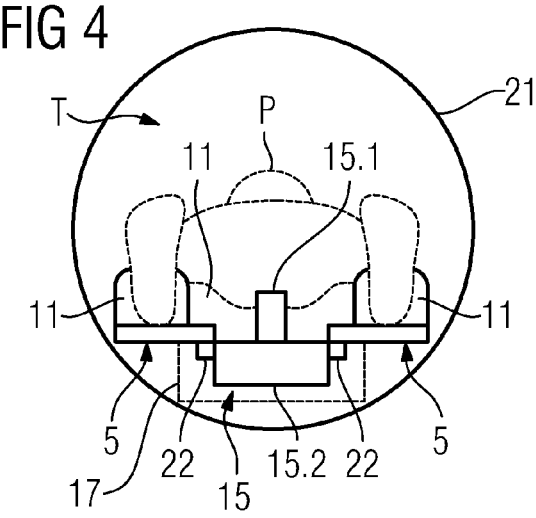

As shown in particular in FIGS. 2 and 4 the medical examination apparatus 15 can also be arranged in the region of the cutout 19 due to the support apparatus 5 being displaced in relation to the patient support table 9 and be secured with securing means 22 arranged on the support apparatus 5 in the region of the cutout 19 in such a manner that the entire cross-section of the patient tunnel T can be utilized for the medical examination apparatus 15. This means that the region below the level of the support apparatus 5 is available for the medical examination apparatus 15 in particular through the cutout 19 and the support apparatus 5 displaced beyond the patient support table 9.

The securing apparatus 22 used can for example be holders arranged on the underside of the support apparatus 5 around the cutout 19, which latch detachably into one another for example or can be connected by means of quick-release clamps for example, engaging with suitable, e.g. form-fit, engagement points on the holding and guiding apparatus 15.2. However other securing apparatuses 22 are also conceivable.

For an examination to be performed by means of the medical examination apparatus 15 and to be monitored using the medical device 1 or to be performed by means of the medical examination apparatus 15 and the medical device 1 the patient support table 9 can be conveyed back toward the front of the medical device 1 without moving the support apparatus 5 in relation to the patient support table 9 in the process. It is thus possible to move the region to be examined in the lower abdomen of the patient P for example into a measuring volume of the medical device 1 in the interior of the patient tunnel T to perform the examination there.

In order to protect the medical examination apparatus 15 attached to the support apparatus 5 reliably from collision with the edge 21 of the patient tunnel T while conveying the patient support table 9 into the interior of the patient tunnel T without further monitoring, the support apparatus 5 also advantageously has a protection apparatus 17, which at least partially encloses the medical examination apparatus 15 secured to the support apparatus 5. In one particularly simple embodiment such a protection apparatus 17 can be configured as trough-shaped or U-shaped, as outlined in FIGS. 2, 3 and 4 with a broken line. The protection apparatus 17 here can be connected in a detachable manner to the support apparatus 5 in the same way as the medical examination apparatus 15. In any case the protection apparatus 17 attached to the support apparatus 5 encloses the medical examination apparatus 15 in particular below, thus defining a framework for the medical examination apparatus 15 that cannot be passed in a downward direction.

After an examination with the medical examination apparatus 15 and the medical device 1 the medical examination apparatus 15 is removed from the support apparatus 5 again and the support apparatus 5 can be displaced with the sliding apparatus 7 into the first position described above, where it can be stopped with the stop apparatus 7.1, in order to be moved out from the patient tunnel T with the patient support table 9 on the front of the medical device 1 in this position. Once outside the patient tunnel T the support apparatus 5 can be lowered again with the patient support table 9, to make it easier for the patient P to climb down.

The invention claimed is:

1. A support apparatus for supporting a patient, comprising:
   a cutout;
   a bearing substructure that supports the support apparatus;
   a sliding apparatus connected to the bearing substructure that moves the support apparatus at least partially beyond the bearing substructure such that the cutout extends beyond the bearing substructure;
   a trough-shaped or U-shaped protection apparatus that can be connected detachably to and below the support apparatus and at least partially encloses a medical examination apparatus, wherein the medical examination apparatus is secured to the support apparatus and can reach the patient through the cutout for performing a medical examination; wherein the medical examination apparatus comprises an apparatus that can be inserted into an abdomen of a patient supported on the support apparatus and a holding and guiding apparatus for the insertable apparatus; and
   wherein the insertable apparatus is selected from the group consisting of: an endorectally insertable biopsy unit, an endovaginally insertable biopsy unit, an endorectally insertable local coil for a magnetic resonance examination, and an endovaginally insertable local coil for the magnetic resonance examination.

2. The support apparatus as claimed in claim 1, wherein the support apparatus is moved beyond the bearing substructure to a position that the cutout is adjacent to the bearing substructure.

3. The support apparatus as claimed in claim 1, wherein the cutout is arranged centrally over a width of the support apparatus and over a length of the support apparatus.

4. The support apparatus as claimed in claim 3, wherein the cutout runs over the length of the support apparatus to a center of the support apparatus.

5. The support apparatus as claimed in claim 3, wherein the cutout runs over the length of the support apparatus to an end of the support apparatus.

6. The support apparatus as claimed in claim 1, wherein the cutout is a slot.

7. The support apparatus as claimed in claim 1, wherein the support apparatus in a region of the cutout comprises a securing apparatus to secure the medical examination apparatus.

8. The support apparatus as claimed in claim 1, wherein the support apparatus comprises a stop apparatus to stop the support apparatus temporarily in relation to the sliding apparatus.

9. The support apparatus as claimed in claim 1, wherein the bearing substructure is a patient support table.

10. The support apparatus as claimed in claim 9, wherein the support apparatus can be attached with the sliding apparatus to an interchangeable board of the patient support table.

11. A patient support table, comprising:
    a cutout;
    a support apparatus that is borne on the patient support table;
    a connecting apparatus that connects the patient support table to the support apparatus;
    a sliding apparatus that is connected to the patient support table and moves the support apparatus at least partially beyond the patient support table such that the cutout extends beyond the patient support table; and
    a trough-shaped or U-shaped protection apparatus that can be connected detachably to and below the support apparatus and at least partially encloses a medical examination, wherein the medical examination apparatus is secured to the support apparatus and can reach the patient through the cutout for performing a medical examination; wherein the medical examination apparatus comprises an apparatus that can be inserted into an abdomen of a patient supported on the support apparatus and a holding and guiding apparatus for the insertable apparatus; and
    wherein the insertable apparatus is selected from the group consisting of: an endorectally insertable biopsy unit, an endovaginally insertable biopsy unit, an endorectally insertable local coil for a magnetic resonance examination, and an endovaginally insertable local coil for the magnetic resonance examination.

12. The patient support table as claimed in claim 11, wherein the connecting apparatus is an interchangeable board.

13. A medical device, comprising:
    a patient tunnel;
    a conveyable patient support table that can be introduced into the patient tunnel;
    a cutout;
    a support apparatus;
    a connecting apparatus that connects the patient support table to the support apparatus;
    a bearing substructure that supports the support apparatus;
    a sliding apparatus that is connected to the bearing substructure and moves the support apparatus at least partially beyond the bearing substructure such that the cutout extends beyond the bearing substructure; and
    a trough-shaped or U-shaped protection apparatus that can be connected detachably to and below the support apparatus and at least partially encloses a medical examination apparatus, wherein the medical examination apparatus is secured to the support apparatus and can reach the patient through the cutout for performing a medical examination; wherein the medical examination apparatus comprises an apparatus that can be inserted into an abdomen of a patient supported on the support apparatus and a holding and guiding apparatus for the insertable apparatus; and
    wherein the insertable apparatus is selected from the group consisting of: an endorectally insertable biopsy unit, an endovaginally insertable biopsy unit, an endorectally insertable local coil for a magnetic resonance examination, and an endovaginally insertable local coil for the magnetic resonance examination.

14. The medical device as claimed in claim 13, wherein the medical device is a magnetic resonance device.

* * * * *